US007001715B2

(12) United States Patent
Houtchens et al.

(10) Patent No.: US 7,001,715 B2
(45) Date of Patent: *Feb. 21, 2006

(54) PURIFICATION OF RED BLOOD CELLS BY SEPARATION AND DIAFILTRATION

(75) Inventors: Robert A. Houtchens, Milford, MA (US); Maria S. Gawryl, East Boston, MA (US); William R. Light, Natick, MA (US); Javed Baqai, Lexington, MA (US)

(73) Assignee: Biopure Corporation, Cambridge, MA (US)

( * ) Notice: Subject to any disclaimer, the term of this patent is extended or adjusted under 35 U.S.C. 154(b) by 404 days.

This patent is subject to a terminal disclaimer.

(21) Appl. No.: 10/090,428

(22) Filed: Feb. 28, 2002

(65) Prior Publication Data

US 2003/0165573 A1 Sep. 4, 2003

(51) Int. Cl.
- A01N 1/02 (2006.01)
- A61K 38/16 (2006.01)
- A61K 35/14 (2006.01)
- C07K 17/00 (2006.01)

(52) U.S. Cl. .......................... 435/2; 424/529; 424/533; 514/6; 530/380; 530/385

(58) Field of Classification Search .................. 424/529, 424/533; 435/2; 514/6; 530/380, 385
See application file for complete search history.

(56) References Cited

U.S. PATENT DOCUMENTS

| | | |
|---|---|---|
| 3,864,478 A | 2/1975 | Bonhard |
| 3,991,181 A | 11/1976 | Doczi |
| 4,001,200 A | 1/1977 | Bonsen et al. |
| 4,001,401 A | 1/1977 | Bonsen et al. |
| 4,053,590 A | 10/1977 | Bonsen et al. |
| 4,061,736 A | 12/1977 | Morris et al. |
| 4,401,652 A | 8/1983 | Simmonds et al. |
| 4,439,357 A | 3/1984 | Bonhard et al. |
| 4,670,417 A | 6/1987 | Iwasaki et al. |
| 4,826,811 A | 5/1989 | Sehgal et al. |
| 4,857,636 A | 8/1989 | Hsia |
| 4,861,867 A | 8/1989 | Estep |
| 5,045,529 A | 9/1991 | Chiang |
| 5,084,558 A | 1/1992 | Rausch et al. |
| 5,189,146 A | 2/1993 | Hsia |
| 5,194,590 A | 3/1993 | Sehgal et al. |
| 5,264,555 A | 11/1993 | Shorr et al. |
| 5,296,465 A | 3/1994 | Rausch et al. |
| 5,296,466 A | 3/1994 | Kilbourn et al. |
| 5,439,882 A | 8/1995 | Feola et al. |
| 5,545,328 A | 8/1996 | Pliura et al. |
| 5,691,452 A | 11/1997 | Gawryl et al. |
| 5,691,453 A | 11/1997 | Wertz et al. |
| 5,753,616 A | 5/1998 | Rausch et al. |
| 5,808,011 A | 9/1998 | Gawryl et al. |
| 5,840,852 A | 11/1998 | Rausch et al. |
| 5,854,209 A | 12/1998 | Jacobs, Jr. et al. |
| 5,895,810 A | 4/1999 | Light et al. |
| 6,518,010 B1 * | 2/2003 | Gawryl et al. .................. 435/2 |
| 2002/0161197 A1 | 10/2002 | Gawryl et al. |

FOREIGN PATENT DOCUMENTS

| | | |
|---|---|---|
| GB | 824375 | 11/1959 |
| SU | 455738 | 1/1975 |
| WO | WO 88/03408 | 5/1988 |
| WO | WO 89/06538 | 7/1989 |
| WO | WO 89/12456 | 12/1989 |
| WO | WO 94/22482 | 10/1994 |
| WO | WO 95/22605 | 8/1995 |
| WO | WO 96/29346 | 9/1996 |
| WO | WO 00/21366 | 4/2000 |

OTHER PUBLICATIONS

Cheung, L.C. et al., "The Preparation of Stroma–Free Hemoglobin by Selective DEAE–Cellulose Absorption," *Analytical Biochemistry*, 137:481–484 (1984).

Cole, Daniel J. et al., "Focal Cerebral Ischemia in Rats: Effect of Hemodilution with α–α Cross–Linked Hemoglobin on CBF," *J. Cereb. Blood Flow MetaB.*, 12(6):971–976 (1992).

De Venuto, F. et al., "Characteristics of stroma–free hemoglobin prepared by crystallization," *J. Lab Clin. Med.*, 89(3):509–516 (1977).

DeVenuto, Frank et al., "Appraisal of Hemoglobin Solution as a Blood Substitute," *Surgery, Gynecology & Obstetrics*, 149(3):417–436 (1979).

Feola, Mario et al., "Development of a Bovine Stroma–Free Hemoglobin Solution as a Blood Substitute," *Surgery, Gynecology & Obstetrics*, 157(5):399–408 (1983).

Gibbs, W. Wayt, "Artificial Blood Quickens," *Scientific American*, [online] [retrieved on Feb. 14, 2001]. Retrieved from Internet: <URL:http://www.sciam.com/0996issue/0996techbus4.html>.

Hamilton, Paul B. et al., "Preparation of Hemoglobin Solutions for Intravenous Infusion," *J. Exp. Med.*, 86:455–463 (1947).

Sehgal, Lakshman R. et al., "Polymerized pyridoxylated hemoglobin: A red cell substitute with normal oxygen capacity," *Surgery*, 95(4):433–438 (1984).

Ritter, Stephen K., "Passing a Blood Test," *Chemical & Engineering*, 76:37–44 (1998).

(Continued)

*Primary Examiner*—Jean C. Witz
(74) *Attorney, Agent, or Firm*—Hamilton, Brook, Smith & Reynolds, P.C.

(57) ABSTRACT

Red blood cells are purified by separating whole blood, such as by centrifugation, to form a red blood cell fraction and a liquid fraction. The whole blood can be defibrinated or treated to prevent coagulation prior to separation. Preferably, the whole blood is bovine blood. The red blood cell fraction is then diafiltered to purify the red blood cells. The purified red blood cells can then be lysed to form a lysate of purified red blood cells. The purified red blood cells and the lysate of purified red blood cells are suitable for use in producing hemoglobin blood substitute.

20 Claims, 1 Drawing Sheet

OTHER PUBLICATIONS

Savitsky, J. Philip et al., "A clinical safety trial of stromafree hemoglobin," *Clin. Pharmacol. Ther.*, 23(1):73–80 (1978).

Sharma, Ajay et al., "An Isologous Porcine Promoter Permits High Level Expression of Human Hemoglobin in Transgenic Swine," *Bio/Technology*,12:55–59 (1994).

Teicher, Beverly A. et al., "Oxygenation of tumors by a hemoglobin solution," *J. Cancer Res. Clin Oncol.*, 120:85–90 (1993).

Alcorta, I. et al., "Influence of the Red Blood Cell Preparation Method on the Efficacy of a Leukocyte Reduction Filter," *Vox Sang*, 71:78–83 (1996).

Baróti Tóth, C. et al., "IgA Content of Washed Red Blood Cell Concentrates," *Vox Sang*, 74:13–14 (1998).

Spain, David A. et al., "Quality Assessment of Intraoperative Blood Salvage and Autotransfusion," *The American Surgeon*, 63(12):1059–1064 (1997).

Bray, P.J. et al., "Defibrination of normal human blood in vitro: a method giving a high recovery of untraumatized cells," *British Journal of Haematology*, 35(4):551–559 (1977). (From Database Medline, 1997, Abstract No. NLM871408.

Kay, H. David et al., "Rapid recovery of non–hemolyzed serum and untraumatized cells by using a new method of blood defibrination in vitro," *J. of Immunological Methods*, 92(2):251–260 (1986).

Topping, David L. et al., "Effects of insulin on the metabolism of the isolated working rat heart perfused with undiluted rat blood," *Biochimica et Biophysica Acta*, 844(2):113–118 (1985).

U.S. Appl. No. 09/795,821, by Maria S. Gawryl, Robert A. Houtchens and William R. Light, filed Feb. 28, 2001.

U.S. Appl. No. 10/306,819, by Maria S. Gawryl, Robert A. Houtchens and William R. Light, filed Nov. 26, 2002.

U.S. Appl. No. 09/460,153, by William R. Light, Maria S. Gawryl, Anthony J. Laccetti and Robert A. Houtchens, filed Dec. 13, 1999.

U.S. Appl. No. 09/349,290, by Maria S. Gawryl, Robert A. Houtchens and William R. Light, filed Jul. 7, 1999.

U.S. Appl. No. 09/912,254, by Maria S. Gawryl, Robert A. Houtchens and William R. Light, filed Jul. 24, 2001.

U.S. Appl. No. 10/018,599, by Maria S. Gawryl, Robert A. Houtchens and William R. Light, filed May 22, 2002.

U.S. Appl. No. 10/018,529, by Maris S. Gawryl, Robert A. Houtchens and William R. Light, filed Jun. 3, 2002.

U.S. Appl. No. Not Assigned Yet, by Edward E. Jacobs, Jr. and Carl W. Rausch, filed Jan. 24, 2003.

* cited by examiner

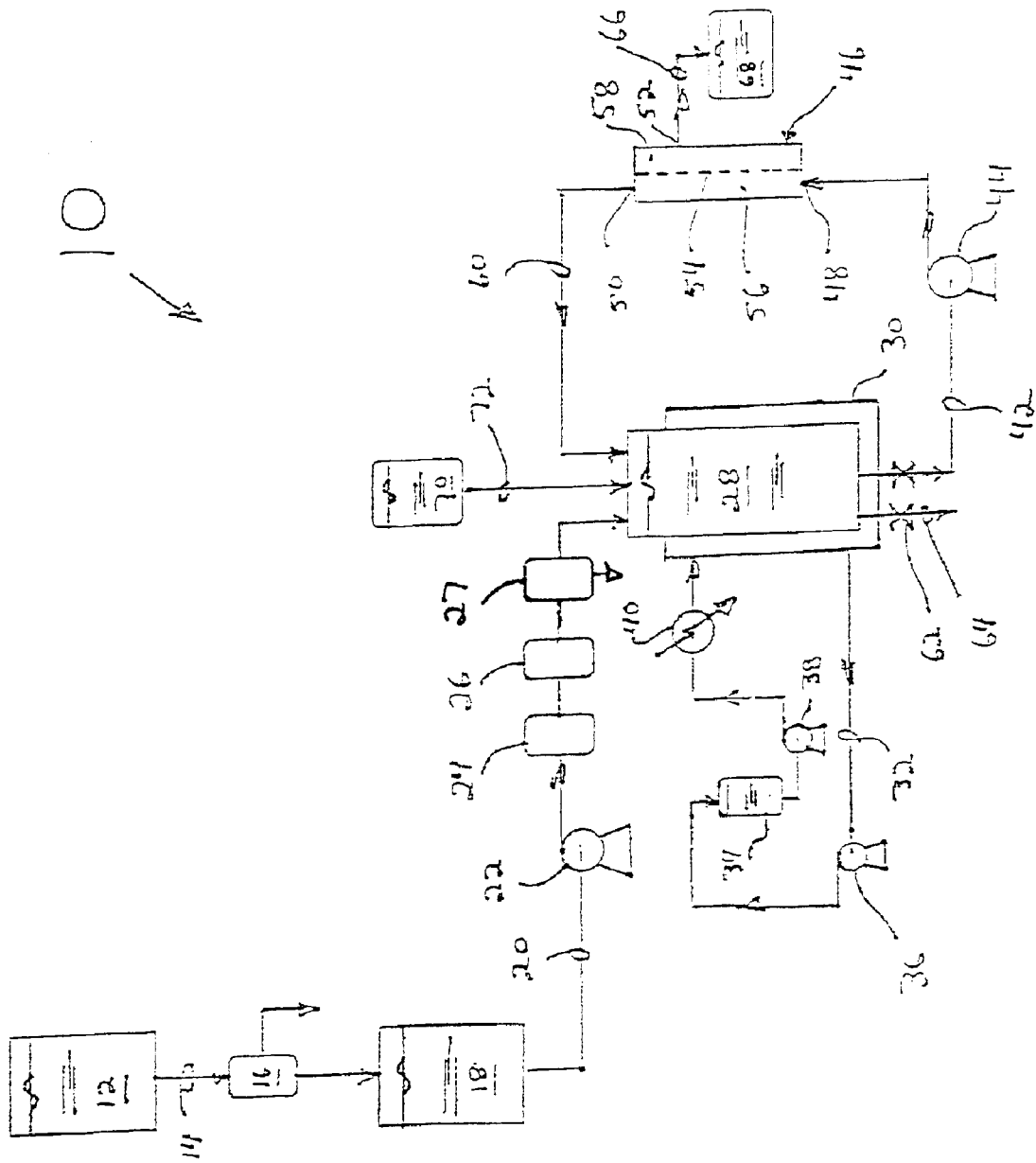

PURIFICATION OF RED BLOOD CELLS BY SEPARATION AND DIAFILTRATION

BACKGROUND OF THE INVENTION

The development of hemoglobin-based oxygen carriers has focused on oxygen delivery for use in medical therapies such as transfusions and the production of blood products. Hemoglobin-based oxygen carriers can be used to prevent or treat hypoxia resulting from blood loss (e.g, from acute hemorrhage or during surgical operations), from anemia (e.g., pernicious anemia or sickle cell anemia), or from shock (e.g, volume deficiency shock, anaphylactic shock, septic shock or allergic shock).

Existing hemoglobin-based oxygen carriers include perfluorochemicals, synthesized hemoglobin analogues, liposome-encapsulated hemoglobin, chemically-modified hemoglobin, and hemoglobin-based oxygen carriers in which the hemoglobin molecules are cross-linked. Preparation of hemoglobin-based oxygen carriers includes several purification steps. In order to remove plasma proteins from whole blood, a process of microfiltration is used to wash the cells of whole blood. The cell washing operation removes plasma proteins from bovine whole blood using diafiltration over a 0.2 $\mu$m microfiltration membrane with isotonic saline/citrate solution. Diafiltration is a continuous filtration operation in which saline/citrate solution is added to the filter retentate to maintain a volume in the recirculation tank. The blood solution is recirculated across the filter and the filtrate, containing the plasma proteins, is sent to waste.

Washing the blood solution using filtration results in highly variable processing times which adversely effect product throughput. Additionally, extended cell washing process times could lead to growth of unacceptable levels of bioburden and to cell lysis, thereby further reducing process yield.

SUMMARY OF THE INVENTION

The invention generally is directed to a method of purifying red blood cells for use in the manufacture of a blood substitute. The method includes separating whole blood, whereby a red blood cell fraction and a liquid fraction are formed. The red blood cell fraction is diafiltered to thereby form purified red blood cells. The purified red blood cells can then be processed further to isolate the hemoglobin molecules.

In one embodiment, the present invention is drawn to forming a lysate of purified red blood cells for use in a hemoglobin blood substitute. The method comprises, separating whole blood, whereby a red blood cell fraction and a liquid fraction are formed. The red blood cell fraction is diafiltered to form purified red blood cells. The purified red blood cells are lysed to form a lysate of purified red blood cells.

In another embodiment, the method includes separating defibrinated whole bovine blood by centrifugation, whereby a red blood cell fraction and a liquid fraction are formed. The red blood cell fraction is diafiltered to thereby form purified red blood cells. The purified red blood cells then are mechanically lysed.

This invention has many advantages. For example, separating of whole blood into a red blood cell fraction and a liquid fraction removes many potential membrane foulants from the resultant red blood cell fraction, allowing more efficient processing of the red blood cell fraction. Specifically, separating whole blood to form a red blood cell fraction and a liquid fraction, and then diafiltering the red blood cell fraction can reduce the period of time necessary to obtain purified red blood cells by diafiltration. Generally, the period of time necessary to diafilter a red blood cell fraction to thereby form purified red blood cells is normalized; the diafiltration period of a red blood cell fraction will approximate more closely the time necessary to diafilter a relatively pure sample of suspended red blood cells. The decrease in time necessary to obtain purified blood cells is obtained with whole blood and defibrinated whole blood. Reduced or normalized cell washing process times reduces the potential for growth of unacceptable levels of bioburden and cell lysis. In turn, the reduction in growth of unacceptable levels of bioburden and cell lysis increases process yield.

BRIEF DESCRIPTION OF THE DRAWINGS

The FIGURE is a schematic representation of apparatus suitable for conducting the method of the invention.

DETAILED DESCRIPTION OF THE INVENTION

The foregoing and other objects, features and advantages of the invention will be apparent from the following more particular description of preferred embodiments of the invention, as illustrated in the accompanying drawing. The drawing is not necessarily to scale, emphasis instead being placed upon illustrating the principles of the invention.

The invention generally is directed to a method of purifying red blood cells by separating whole blood into a red blood cell fraction and a liquid fraction. Potential membrane foulants are believed to be partitioned from a resulting red blood cell fraction. A liquid fraction that includes a substantial portion of the foulants, and which is formed by fractionating the whole blood, is separated from the red blood cell fraction and the red blood cell fraction then is diafiltered.

Referring to the Figure, shown therein is apparatus 10, which is one embodiment of an apparatus suitable for practicing the method of the invention. Whole blood is collected in vessel 12. Whole blood suitable for use in the invention can be freshly collected or collected from otherwise outdated sources, such as expired human blood from a blood bank. Further, the whole blood can have been maintained in a frozen and/or a liquid state, although it is preferred that the whole blood not be frozen prior to use in this method. Examples of suitable sources of whole blood include human, bovine, ovine, porcine, other vertebrates and transgenically-produced hemoglobin, such as the transgenic Hb described in *BIO/TECHNOLOGY,* 12:55–59 (1994), the teachings of which are incorporated herein by reference in their entirety. The whole blood can be collected from live or freshly slaughtered animal donors. One method for collecting bovine blood is described in U.S. Pat. Nos. 5,084,558 and 5,296,465, issued to Rausch, et al., the teachings of which are incorporated by reference in their entirety.

In one embodiment, the whole blood is defibrinated in vessel 12 by a suitable method. Defibrination can be accomplished as described in U.S. application Ser. No. 09/795,821 by Gawryl, et al., filed on Feb. 28, 2001, the teachings of which are incorporated herein in their entirety. Defibrinating the blood initiates the clotting cascade, artificially removing the fibrin molecules involved in the formation of blood clots. Defibrination can be induced by chemical or mechanical means. Chemical coagulating agents are defined herein as substances that induce clotting. For example, collagen induces coagulation, so that when there is an external wound, a fibrin clot will stop blood from flowing. Artificially exposing blood to collagen will cause the formation of fibrin clots, which can be removed to produce defibrinated blood. Examples of other coagulating agents are tissue extract, tissue factor, tissue thromboplastin, anionic phospholipid, calcium, negatively charged materials (e.g., glass, kaolin, some synthetic plastics, fabrics). A preferred clotting agent is collagen. The liquid fraction obtained by separating blood cells from defibrinated whole blood typically is referred to as "plasma."

The whole blood can be exposed to the clotting agent for a period of time sufficient to cause essentially all fibrin in the blood to be converted into a fibrin clot. The appropriate time is determined by the point at which fibrin molecules apparently stop polymerizing. Chemical defibrination, defined herein as defibrination that is induced by exposure to a chemical coagulating agent, is conducted at a suitable temperature, preferably a temperature in a range of between about 4° C. and about 40° C.

In another embodiment, mechanical agitation, such as stirring, can also be used to initiate the clotting cascade. The whole blood can be stirred until fibrin polymerization apparently ceases. The accumulated fibrin is removed to complete defibrination. Mechanical defibrination, defined herein as defibrination induced by agitating the blood solution, is conducted at a suitable temperature, and preferably at a temperature in a range of between about 4° C. and about 40° C.

In an alternative embodiment, the whole blood can be treated to prevent coagulation. For example, the whole blood can be treated with an anti-coagulation agent such as sodium citrate, heparin, ethylenediaminetetraacetic acid (EDTA) and sodium oxylate used at concentrations sufficient to inhibit coagulation of the whole blood. In one embodiment, 5 L of sodium citrate(34 g/l) is added to 15 L of freshly collected whole blood to yield a final concentration of 8.5 g/l citrate in the whole blood solution. In another embodiment, EDTA is added to the freshly isolated whole blood to yield a final concentration of 0.18%. The liquid fraction obtained by separating blood cells from whole blood treated with anticoagulants typically is referred to as "serum."

It is also possible to defibrinate blood that already has been citrated by saturating the citrated blood with a divalent cation, and then defibrinating the solution, similar to the means by which noncitrated blood would be processed. The preferred divalent cation is calcium.

Where the blood has been treated to induce coagulation, fibrin clots are removed from the whole blood by suitable means. An example of a suitable means is shown in the Figure. The whole blood, including the fibrin and fibrin clots, is directed from vessel 12, through the line 14 and strainer 16. A 60 mesh screen is an example of a suitable strainer. Optionally, or alternatively to the use of a strainer, cheesecloth or polypropylene filters can be employed to remove large debris, including fibrin clots. The fibrin clots are collected at strainer 16 and the remainder of the whole blood is directed to vessel 18.

Where the blood is treated with an anticoagulant, the treated blood can be directed to centrifuge 27, bypassing line 14, strainer 16, vessel 18, line 20, pump 22 filter 24 and filter 26. However, the treated blood can also be directed through line 14, strainer 16, vessel 18, line 20, pump 22 filter 24 and filter 26. Directing the anticoagulant-treated whole blood through strainer 16 and filters 24 and 26 is useful to remove any large debris present in the treated whole blood.

As shown in the Figure, whole blood (either treated to induce coagulation or not) is directed from vessel 18 through line 20 by pump 22 and through first filter 24 and second filter 26 to centrifuge 27. In one embodiment, first filter 24 and second filter 26 are polypropylene filters. In a particularly preferred embodiment, first filter 24 has a permeability of about 800 $\mu$m, and second filter 26 has a permeability of about 50 $\mu$m. Where the whole blood has been treated to initiate the clotting cascade, removal of essentially all of the fibrin by first filter 24 and second filter 26 completes the defibrination step.

After filter 26, the whole blood, either defibrinated or not, is subjected to separation to form a red blood cell fraction and a liquid fraction. "Separation," also referred to herein as "fractionation," includes partitioning of red blood cells from serum or plasma to form a separate liquid fraction which is preferably the serum or plasma, respectively. The separation techniques as used herein generally are based on separation by density, such as by centrifugation, as distinguished from separation based on concentration or size and concentration, such as by diafiltration.

As used herein, "liquid fraction" includes liquid resulting from separation of whole blood and separation of whole blood that has been defibrinated. In one embodiment, the liquid fraction is "plasma," e.g., the liquid fraction resulting from the separation of defibrinated whole blood. In another embodiment, the liquid fraction is "serum," e.g., the liquid fraction resulting from the separation of whole blood that has been treated to prevent coagulation. In one embodiment, the whole blood has been treated with anticoagulants such as sodium citrate or heparin.

In one embodiment, after filter 26, the whole blood, either defibrinated or not, is subjected to separation in centrifuge 27. Typically, during centrifugation, the whole blood is exposed to a G-force in a range of between about 1,000 and about 12,000×G in order to separate the whole blood and thereby form the red blood cell fraction (blood cell component) and the liquid fraction. Typically, centrifugation is conducted over a period of time in a range of between about 30 seconds and about 4 minutes. Preferably, the centrifugation is conducted at about 8,000–10,000×G for about 3 minutes. The temperature of the whole blood during the separation step generally is in a range of between about 4 and about 15° C.

In one embodiment, the red blood cell fraction includes red blood cells and white blood cells of the whole blood and the liquid fraction includes the platelets of the whole blood. Also, preferably, the red blood cell fraction includes most of the red blood cells (RBCs) (e.g., at least about 90%, or at least about 95%, or at least about 99%) of the whole blood.

The liquid fraction is substantially removed from the red blood cell fraction. Typically, the liquid fraction is removed from the red blood cell fraction simultaneously with centrifugation. In one embodiment, the liquid fraction is continuously removed during centrifugation using, for example, a tubular bowl centrifuge in continuous feed mode. In another embodiment, a tubular bowl centrifuge can be used in a batch mode. In another embodiment, the liquid fraction is removed from the red blood cell fraction after separation of the red blood cell fraction and the liquid fraction by decanting the liquid fraction from the red blood cell fraction.

The red blood cell fraction is directed from centrifuge 27 to vessel 28 of the Figure. The red blood cell fraction is suspended in a suitable solution (e.g., diafiltration buffer) in vessel 28. Acceptable isotonic solutions are known in the art and include solutions, such as a citrate/saline solution, having a pH and osmolarity which does not rupture the cell membranes of red blood cells and which displaces the liquid portion of the whole blood. A preferred isotonic solution has a neutral pH and an osmolarity between about 285–315 mOsm. An example of a suitable solution is an isotonic citrate/saline buffer (sodium citrate dehydrate -6.0 g/L, sodium chloride -8.0 g/L). In an alternative embodiment, the red blood cell fraction can be resuspended in any suitable isotonic solution, for example, 5% dextrose. The red blood cell fraction can be resuspended at a concentration of about 20 to about 200 g/l.

In one embodiment, the red blood cell fraction is suspended in a volume of isotonic solution such that the original volume of the whole blood from which the red blood cell fraction was obtained is restored. The resuspended blood cell fraction is hereinafter referred to as a "blood solution."

The blood solution is maintained at a suitable temperature in vessel 28. Preferably, the blood solution is maintained at a temperature in a range of between about 4° C. and about 15° C. The temperature of blood solution in vessel 28 is maintained by recirculation of a suitable medium, such as ethylene glycol, through jacket 30 at vessel 28. Recirculation of medium through jacket 30 is maintained by line 32, reservoir 34, pumps 36, 38 and a chiller, or refrigeration unit, 40.

Thereafter, the blood solution is filtered, thereby purifying the red blood cells. Preferably, the blood solution is filtered by diafiltration. In one embodiment, diafiltration is conducted by directing the blood solution from vessel 28 through line 42 and pump 44 to diafiltration module 46. Diafiltration module 46 includes inlet 48, retentate outlet 50 and permeate outlet 52. Membrane 54 partitions retentate portion 56 of diafiltration module 46 from permeate portion 58 of diafiltration module 46. Preferably, membrane 54 has a permeability limit in a range of between about 0.01 $\mu$m and about 5 $\mu$m. In one embodiment, the blood solution is diafiltered across a membrane having a permeability limit in the range of between 0.2 $\mu$m and about 2.0 $\mu$m. Alternate suitable diafilters include microporous membranes with pore sizes that will separate RBCs from substantially smaller blood solution components, such as a 0.1 $\mu$m to 0.5 $\mu$m filter (e.g., a 0.2 $\mu$m hollow fiber filter, Microgon Krosflo II microfiltration cartridge, Laguna Hills, Calif.). In an especially preferred embodiment, membrane 54 has a permeability limit in a range of between about 0.1 and about 2 $\mu$m.

A portion of the liquid component of the blood solution in diafiltration module 46 passes across membrane 54 from retentate portion 56 to permeate portion 58, thereby purifying red blood cells of retentate portion 56. Components of the blood solution, such as plasma, or components which are significantly smaller in diameter than RBCs pass through the walls of the diafilter forming a filtrate.

Purified red blood cells of the blood solution are directed through retentate outlet 50 and line 60 back to vessel 28. Purified red blood cells can be collected from vessel 28 through valve 62 to line 64 for further processing. The membrane permeable liquid component contains any remaining liquid fraction of the whole blood (e.g., plasma or serum) and diafiltration buffer. The liquid component that permeates membrane 54 can be directed from permeate portion 58 of diafiltration module 46 through line 66 and collected from vessel 68. Blood solution recirculating through vessel 28 and diafiltration module 46 can be sampled at sampling ports (not shown) in line 42 or line 60.

Preferably, while diafiltering the blood solution to wash the red blood cells, a liquid, such as an isotonic solution, is directed from vessel 70 through line 72 to the blood solution in vessel 28 to dilute the concentration of the blood solution. In one embodiment, the blood solution is diluted to a concentration in a range of between about 25% and about 75% of the initial suspended concentration of red blood cells, by volume. Concentration during diafiltration then can reduce the volume back to the original concentration or higher. Generally, the process of adding a liquid to the suspended red blood cells and then removing at least a portion of the liquid is referred to as "cell washing." Preferably, the isotonic solution includes an ionic solute or is aqueous. Suitable istonic solutions are described above. In an alternate embodiment, the blood is washed through a series of sequential (or reverse sequential) dilution and concentration steps, wherein the blood solution is diluted by adding at least one isotonic solution, and is concentrated by flowing across a filter, thereby forming a dialyzed blood solution.

The red blood cells of the blood solution generally are washed described above, to separate red blood cells from residual extracellular plasma proteins, such as serum albumins or antibodies (e.g., immunoglobulins (IgG)) left in the red blood cell fraction. The result is a reduction in the amount of microfiltration membrane-permeable species (including membrane-permeable plasma proteins) in the blood solution.

Cell washing generally is considered to be complete when the level of plasma or serum proteins contaminating the red blood cells has been substantially reduced (typically by at least about 90% of the plasma or serum proteins present in the red blood cell fraction prior to washing). Additional washing may further separate extracellular plasma proteins from the RBCs. For instance, diafiltration with six volumes of isotonic solution may be sufficient to remove at least about 99% of IgG from the blood solution.

The method of the present invention reduces the presence of potential membrane foulants that can slow manufacturing runs. For example, small fibrin molecules can be problematic and may foul a membrane filter if they accumulate on the surface of a membrane with a permeability of 0.1 to 5 $\mu$m and thus block the pores. A narrower range in which the foulants can be problematic is 0.2 to 0.4 $\mu$m. However, as shown in Example 4, fibrin alone does not account for all of the potential membrane foulants. As shown in Example 4, in 2 out of 3 experiments, defibrinated whole blood had cell washing process times of greater than 100 minutes. However, the red blood cell fraction generated from the same volume of defibrinated whole blood and diluted to the original volume in isotonic buffer had cell washing times of 45 minutes or less.

Furthermore, defibrination can cause some red blood cell lysing. Red blood cells, white blood cells, or platelets that have broken open can stick to the filter. It is believed that fractionating whole blood and separating a red blood cell fraction from a liquid fraction removes a significant portion of such potential foulants, thereby normalizing the time required to diafilter, or "wash," red blood cells to purify them for use in the manufacture of a blood substitute.

To prepare a hemoglobin blood substitute from the purified red blood cells, the purified red blood cells of the washed blood solution can be processed further to isolate the hemoglobin molecules. The resulting washed blood solution can be exposed to means for separating red blood cells in the washed blood solution from white blood cells and platelets, such as by centrifugation. It is understood that other methods generally known in the art for separating red blood cells from other blood cell components can be employed. For example, one embodiment of the invention separates red blood cells by sedimentation, wherein the separation method does not rupture the cell membranes of a significant amount of the RBCs, such as less than about 5% of the RBCs, prior to red blood cell separation from the other blood components.

Following separation of the red blood cells from the other components of the washed red blood cell fraction, the RBCs are lysed, resulting in the production of a hemoglobin (Hb) solution. Methods of lysis include mechanical lysis, chemical lysis, hypotonic or osmotic lysis or other known lysis methods which release hemoglobin without significantly damaging the ability of the Hb to transport and release oxygen.

Following lysis, the lysed red blood cell phase is then ultrafiltered to remove larger cell debris, such as proteins with a molecular weight above about 100,000 Daltons. The hemoglobin is then separated from the non-Hb components of the filtrate.

Methods of ultrafiltration and methods of separating Hb from non-Hb components by pH gradients and chromatography are further described in U.S. Pat. No. 5,691,452, which is incorporated by reference in its entirety.

Preferably, the Hb eluate then is deoxygenated prior to polymerization to form a deoxygenated Hb solution (hereinafter deoxy-Hb) for further processing into a hemoglobin-based oxygen carrier. In a preferred embodiment, deoxygenation substantially deoxygenates the Hb without significantly reducing the ability of the Hb in the Hb eluate to transport and release oxygen, such as would occur from formation of oxidized hemoglobin (metHb). Alternatively, the hemoglobin solution may be deoxygenated by chemical scavenging with a reducing agent selected from the group consisting of N-acetyl-L-cysteine (NAC), cysteine, sodium dithionite or ascorbate. A suitable method of deoxygenation is described in U.S. Pat. No. 5,895,810, filed Jun. 7, 1995, which is incorporated herein by reference in its entirety.

The deoxygenated hemoglobin solution can be further processed into a hemoglobin-based oxygen carrier. As defined herein, a "hemoglobin-based oxygen carrier" is a hemoglobin-based composition suitable for use in humans, mammals, and other vertebrates, which is capable of transporting and transferring oxygen to vital organs and tissues, at least, and can maintain sufficient intravascular oncotic pressure, wherein the hemoglobin has been isolated from red blood cells. "Vertebrate" includes humans, or any other vertebrate animals which use blood in a circulatory system to transfer oxygen to tissue.

"Stable polymerized hemoglobin," as defined herein, is a component of a hemoglobin-based oxygen carrier composition which does not substantially increase or decrease in molecular weight distribution and/or in methemoglobin content during storage periods at suitable storage temperatures for periods of about two years or more. Suitable storage temperatures for storage of one year or more are between about 0° C. and about 40° C. The preferred storage temperature range is between about 0° C. and about 25° C.

A suitable low oxygen environment, or an environment that is substantially oxygen-free, is defined as the cumulative amount of oxygen in contact with the hemoglobin-based oxygen carrier, over a storage period of at least about two months, preferably at least about one year, or more preferably at least about two years, which will result in a methemoglobin concentration of less than about 15% by weight in the hemoglobin-based oxygen carrier. The cumulative amount of oxygen includes the original oxygen content of the hemoglobin-based oxygen carrier and packaging in addition to the oxygen resulting from oxygen-leakage into the hemoglobin-based oxygen carrier packaging.

Throughout this method, from RBC collection until hemoglobin polymerization, blood solution, RBCs and hemoglobin are maintained under conditions sufficient to minimize microbial growth, or bioburden, such as maintaining temperature at less than about 20° C. and above 0° C. Preferably, temperature is maintained at a temperature of about 15° C. or less. More preferably, the temperature is maintained at 10±2° C.

In this method, portions of the components for the process of preparing a stable polymerized hemoglobin-based oxygen carrier are sufficiently sanitized to produce a sterile product. "Sterile" is as defined in the art, specifically, in the United States Pharmacopeia requirements for sterility provided in USP XXII, Section 71, pages 1483–1488. Further, portions of components that are exposed to the process stream, are usually fabricated or clad with a material that will not react with or contaminate the process stream. Such materials can include stainless steel and other steel alloys, such as Hasteloy.

In one embodiment, polymerization results from intramolecular cross-linking of Hb. The amount of a sulfhydryl compound mixed with the deoxy-Hb is high enough to increase intramolecular cross-linking of Hb during polymerization and low enough not to significantly decrease intermolecular cross-linking of Hb molecules, due to a high ionic strength. Typically, about one mole of sulfhydryl functional groups (—SH) are needed to oxidation-stabilize between about 0.25 moles to about 5 moles of deoxy-Hb.

Optionally, prior to polymerizing the oxidation-stabilized deoxy-Hb, an appropriate amount of water is added to the polymerization reactor. In one embodiment, an appropriate amount of water is that amount which would result in a solution with a concentration of about 10 to about 100 g/l Hb when the oxidation-stabilized deoxy-Hb is added to the polymerization reactor. Preferably, the water is oxygen-depleted.

The temperature of the oxidation-stabilized deoxy-Hb solution in the polymerization reactor is raised to a temperature to optimize polymerization of the oxidation-stabilized deoxy-Hb when contacted with a cross-linking agent. Typically, the temperature of the oxidation-stabilized deoxy-Hb is about 25 to about 45° C., and preferably about 41 to about 43° C. throughout polymerization. An example of an acceptable heat transfer means for heating the polymerization reactor is a jacketed heating system which is heated by directing hot ethylene glycol through the jacket.

The oxidation-stabilized deoxy-Hb is then exposed to a suitable cross-linking agent at a temperature sufficient to polymerize the oxidation-stabilized deoxy-Hb to form a solution of polymerized hemoglobin (poly(Hb)) over a period of about 2 hours to about 6 hours. A suitable amount of a cross-linking agent is that amount which will permit intramolecular cross-linking to stabilize the Hb and also intermolecular cross-linking to form polymers of Hb, to thereby increase intravascular retention. Typically, a suitable amount of a cross-linking agent is that amount wherein the molar ratio of cross-linking agent to Hb is in excess of about 2:1. Preferably, the molar ratio of cross-linking agent to Hb is between about 20:1 to 40:1.

Examples of suitable cross-linking agents include polyfunctional agents that will cross-link Hb proteins, such as glutaraldehyde, succindialdehyde, activated forms of polyoxyethylene and dextran, α-hydroxy aldehydes, such as glycolaldehyde, N-maleimido-6-aminocaproyl-(2'-nitro,4'-sulfonic acid)-phenyl ester, m-maleimidobenzoic acid-N-hydroxysuccinimide ester, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxysulfosuccinimide ester, N-succinimidyl(4-iodoacetyl)aminobenzoate, sulfosuccinimidyl(4-iodoacetyl)aminobenzoate, succinimidyl 4-(p-maleimidophenyl)butyrate, sulfosuccinimidyl 4-(p-maleimidophenyl)butyrate, 1-ethyl-3-(3-dimethylaminopropyl)carbodiimide hydrochloride, N,N'-phenylene dimaleimide, and compounds belonging to the bis-imidate class, the acyl diazide class or the aryl dihalide class, among others.

Poly(Hb) is defined as having significant intramolecular cross-linking if a substantial portion (e.g., at least about 50%) of the Hb molecules are chemically bound in the poly(Hb).

In a preferred embodiment, glutaraldehyde is used as the cross-linking agent. Typically, about 10 to about 70 grams of glutaraldehyde are used per kilogram of oxidation-stabilized deoxy-Hb. More preferably, glutaraldehyde is added over a period of five hours until approximately 29–31 grams of glutaraldehyde are added for each kilogram of oxidation-stabilized deoxy-Hb.

Wherein the cross-linking agent used is not an aldehyde, the poly(Hb) formed is generally a stable poly(Hb). Wherein the cross-linking agent used is an aldehyde, the poly(Hb) formed is generally not stable until mixed with a suitable reducing agent to reduce less stable bonds in the poly(Hb) to form more stable bonds. Examples of suitable reducing agents include sodium borohydride, sodium cyanoborohydride, sodium dithionite, trimethylamine, t-butylamine, morpholine borane and pyridine borane. The poly(Hb) solution is optionally concentrated by ultrafiltration until the concentration of the poly(Hb) solution is increased to between about 75 and about 85 g/l. For example, a suitable ultrafilter is a 30,000 Dalton filter (e.g., Millipore® Helicon™ Cat # CDUF050LT; Amicon® Cat # 540430, Bedford, Mass.).

The pH of the poly(Hb) solution is then adjusted to the alkaline pH range to preserve the reducing agent and to prevent hydrogen gas formation, which can denature Hb during the subsequent reduction. The poly(Hb) is typically purified to remove non-polymerized hemoglobin. This can be accomplished by diafiltration or hydroxyapatite chromatography (see, e.g. U.S. Pat. No. 5,691,453, filed Jun. 7, 1995, which is incorporated herein by reference in its entirety). Following pH adjustment, at least one reducing agent, preferably a sodium borohydride solution, is added to the polymerization step. The pH and electrolytes of the stable poly(Hb) can then be restored to physiologic levels to form a stable polymerized hemoglobin-based oxygen carrier, by diafiltering the stable poly(Hb) with a diafiltration solution having a suitable pH and physiologic electrolyte levels.

Suitable methods of cross-linking hemoglobin and preserving the hemoglobin-based oxygen carrier are discussed in detail in U.S. Pat. 5,691,452, issued Nov. 25, 1997, which is incorporated herein by reference in its entirety.

Vertebrates that can receive the hemoglobin-based oxygen carrier, formed by the methods of the invention, include mammals, such as humans, non-human primates, dogs, cats, rats, horses, or sheep. Further, vertebrates, that can receive said hemoglobin-based oxygen carrier, include fetuses (prenatal vertebrate), post-natal vertebrates, or vertebrates at time of birth.

A hemoglobin-based oxygen carrier of the present invention can be administered into the circulatory system by injecting the hemoglobin-based oxygen carrier directly and/or indirectly into the circulatory system of the vertebrate, by one or more injection methods. Examples of direct injection methods include intravascular injections, such as intravenous and intra-arterial injections, and intracardiac injections. Examples of indirect injection methods include intraperitoneal injections, subcutaneous injections, such that the hemoglobin-based oxygen carrier will be transported by the lymph system into the circulatory system or injections into the bone marrow by means of a trocar or catheter. Preferably, the hemoglobin-based oxygen carrier is administered intravenously.

The vertebrate being treated can be normovolemic, hypervolemic or hypovolemic prior to, during, and/or after infusion of the hemoglobin-based oxygen carrier. The hemoglobin-based oxygen carrier can be directed into the circulatory system by methods such as top loading and by exchange methods.

A hemoglobin-based oxygen carrier can be administered therapeutically, to treat hypoxic tissue within a vertebrate resulting from many different causes including anemia, shock, and reduced RBC flow in a portion of, or throughout, the circulatory system. Further, the hemoglobin-based oxygen carrier can be administered prophylactically to prevent oxygen-depletion of tissue within a vertebrate, which could result from a possible or expected reduction in RBC flow to a tissue or throughout the circulatory system of the vertebrate. Further discussion of the administration of hemoglobin to therapeutically or prophylactically treat hypoxia, particularly from a partial arterial obstruction or from a partial blockage in microcirculation, and the dosages used therein, is provided in U.S. Pat. 5,854,209, filed Mar. 23, 1995, which is incorporated herein by reference in its entirety.

Typically, a suitable dose, or combination of doses of hemoglobin-based oxygen carrier, is an amount which when contained within the blood plasma will result in a total hemoglobin concentration in the vertebrate's blood between about 0.1 to about 10 grams Hb/dl, or more, if required to make up for large volume blood losses.

The invention will now be further and specifically described by the following examples.

EXEMPLIFICATION

Example 1

Bench Scale Experiment

Referring to the Figure, whole bovine blood was collected into a container with anticoagulant (EDTA) and was subjected to centrifugation at 2,600 rpm (1,200×G) for 30 minutes at 4° C. in centrifuge 27 (Beckman J2-21 using a JA-10 rotor) which separated the whole blood into a heavy phase (red blood cell fraction, or cell component) and a light phase (liquid fraction). The starting volume of blood was 200 ml. The red blood cell fraction and liquid fraction were separated and each phase was processed in a bench-scale cell washing system. The liquid fraction was processed directly. The red blood cell fraction was directed to a recirculation vessel, 28, and diluted with isotonic citrate/saline buffer (sodium citrate dehydrate 6.0 g/L, sodium chloride 8 g/L) to its original volume. The recirculation vessel was kept at the appropriate temperature by recirculation of a suitable medium in a recirculation jacket, 30, surrounding the recirculation vessel. The diluted red blood cell fraction, (e.g., blood solution) was directed through a filter module, 46, (Microgon Minikros sampler) to separate the blood solution into a permeate and a retentate. The permeate was collected in a graduated cylinder. The retentate was directed back to recirculating vessel through line 60. Pressure was monitored through a pressure input pressure gauge (0–30 PSI) in line 42 and outlet pressure gauge (0–15 PSI) in line 60. The cell component was washed with isotonic citrate/saline buffer in the bench-scale system until 400 ml of membrane permeate (2 retentate volumes) were obtained. The data is summarized in Table 1.

TABLE 1

| Sample | Time to Collect 400 ml Permeate (min:sec) |
|---|---|
| Red Blood Cell Fraction | 34:58 |
| Liquid Fraction | 52:20 |

As can be seen from Table 1, the liquid fraction contains a microfiltration membrane foulant, because the processing of the liquid fraction was slower than the processing of the red blood cell fraction.

Example 2

Bench Scale Experiment II

Bovine blood was collected into sanitized stainless steel containers containing sodium citrate anti-coagulant and subjected to batch centrifugation in a second centrifuge type, a CEPA Tubular Bowl Centrifuge (New Brunswick Scientific Co, Edison, N.J.) to generate a red blood cell fraction and a liquid fraction. The centrifuge was operated in two feed configurations. In one configuration, the feed was pumped in with a peristaltic pump and in the second configuration the blood was added using siphoning. The red blood cell fraction obtained from each configuration was than diluted to the original volume of the bovine blood, to generate blood solution with isotonic citrate/saline buffer. As a control, citrated whole blood without centrifugation was included as a separate sample. The samples were washed in a bench scale washing apparatus until three retentate volumes of permeate was obtained (about 600 ml). The data is summarized in Table 2.

TABLE 2

| Experiment Designation | Blood Centrifuge Loading Method | Time to Collect 600 ml Permeate |
|---|---|---|
| Centrifuge #1 | Peristaltic Pump | 36:56 |
| Centrifuge #2 | Siphon | 38:08 |
| Citrated Control | Not Centrifuged | 1:20:53 |

As can be seen in Table 2, centrifugation, which resulted in removal of the liquid fraction from the red blood cell fraction increased the speed of cell washing.

Example 3

Pilot Scale Experiment

Blood was pooled from three animals and treated with anticoagulant as described in Example 2. The treated pooled blood was centrifuged in either a Westfalia (Northvale, N.J.) SA-1 or SB-7 centrifuge, to generate a red blood cell fraction and a liquid fraction, or washed directly as a control. The red blood cell fraction was washed using a pilot scale washing system.

The red blood cell fraction was directed through a strainer using a pump (Watson-Marlow pump, Wilmington, Mass.). After passing through the strainer, the red blood cell fraction was directed into a recirculation vessel and diluted with isotonic citrate/saline buffer. The volume of the recirculation vessel was 9.6 liters. The recirculation vessel was kept at the appropriate temperature by recirculation of ethylene glycol through a recirculation jacket surrounding the recirculation vessel. The red blood cell fraction/buffer mixture was directed through a filter (Microgon) using a pump (Waukesha, Delavan, Wis.) to separate the red blood cell fraction/buffer mixture into permeate and retentate. The permeate was directed to a permeate collection container on a floor scale. The retentate was directed back to the recirculating vessel. Pressure was monitored using a feed pressure gauge and a retentate pressure gauge. A total of three diafiltration volumes were passed over the retained cells. The data is summarized in Table 3.

TABLE 3

| Sample | Processing Time (min) |
|---|---|
| Citrated Whole Blood Control (1) | 285 |
| Citrated Whole Blood Control (2) | >400 |
| Red Blood Cell Fraction Westfalia SA-1 (1) | 88 |
| Red Blood Cell Fraction Westfalia SA-1 (2) | 72 |
| Red Blood Cell Fraction Westfalia SB-7 (1) | 134 |
| Red Blood Cell Fraction Westfalia SB-7 (2) | 141 |

As can be seen from Table 3, the red blood cell fraction from blood centrifuged either in the SA-1 or SB-7 centrifuge had greatly reduced processing time compared to citrated whole blood. While not wishing to be bound by theory, cell washing time was decreased by a greater amount when the whole blood was centrifuged in the SA-1 centrifuge as compared to the SB-7 because the SB-7 caused significant lysis of the cells, the stroma of which can cause microfilter membrane fouling.

Example 4

Effect of Defibrination on Process Time With and Without Centrifugation

Approximately 4 liters of blood from two cows were pooled and defibrinated by mechanical agitation. The blood contained approximately 400 g of hemoglobin. The resulting defibrinated blood contained 12 g/L hemoglobin. The defibrinated blood was either centrifuged, resulting in a red blood cell fraction with approximately 5–10% of the plasma remaining, or not centrifuged. The defibrinated red blood cell fraction and defibrinated whole blood were washed as described in Example 3, except that five diafiltration volumes were collected. The starting volume for both samples was 7 liters.

TABLE 4

| Sample | Process Time (min) |
|---|---|
| Centrifuged Defibrinated Blood (1) | 37 |
| Defibrinated Whole Blood - Control (1) | 28 |
| Centrifuged Defibrinated Blood (2) | 45 |
| Defibrinated Whole Blood - Control (2) | 150 |
| Centrifuged Defibrinated Blood (3) | 25 |
| Defibrinated Whole Blood - Control (3) | 135 |

In the first experiment shown in Table 4, the rate of cell washing of both defibrinated red blood cell fraction and defibrinated whole blood was very rapid and centrifugation did not improve the process time. However, in experiments 2 and 3, the rate of cell washing was improved for the defibrinated red blood cell fraction compared to the defibrinated whole blood, demonstrating that the membrane foulant was not removed by defibrination. Therefore, centrifugation improves cell washing performance for both whole blood and blood that has been defibrinated.

Equivalents

Those skilled in the art will recognize, or be able to ascertain using no more than routine experimentation, many equivalents to the specific embodiments of the invention described herein. These and all other such equivalents are intended to be encompassed by the following claims.

What is claimed is:

1. A method of purifying red blood cells, comprising the steps;
   a) separating defibrinated whole blood, whereby a red blood cell fraction and a liquid fraction are formed; and
   b) diafiltering the red blood cell fraction to thereby form purified red blood cells.

2. The method of claim 1, wherein the whole blood is separated by sedimentation of red blood cells in the whole blood.

3. The method of claim 2, wherein the sedimentation of red blood cells is obtained by centrifuging the whole blood.

4. The method of claim 3, wherein the centrifugation of the whole blood causes the red blood cell fraction to consist essentially of red blood cells.

5. The method of claim 1, wherein the whole blood is fractionated by exposing the whole blood to a G-force in a range of between about 10×G and about 12,000×G.

6. The method of claim 1, wherein the liquid fraction is removed from the from the red blood cell fraction by decanting after step a).

7. The method of claim 1, wherein the liquid fraction is removed from the red blood cell fraction simultaneously with separation of the liquid fraction and the red blood cell fraction.

8. The method of claim 1, wherein the whole blood is defibrinated mechanically.

9. The method of claim 1, further including the step of lysing the purified red blood cells.

10. The method of claim 9, wherein the purified red blood cells are lysed mechanically.

11. The method of claim 9, wherein the purified red blood cells are lysed osmotically.

12. The method of claim 1, wherein the red blood cell fraction includes most of the white cells and platelets of the whole blood.

13. The method of claim 1, wherein the red blood cell fraction is diafiltered with a membrane having a permeability in a range of between about 0.1 $\mu$m and about 5 $\mu$m.

14. The method of claim 1, wherein the whole blood is bovine whole blood.

15. A method of forming a lysate of purified red blood cells for use in a hemoglobin blood substitute, comprising the steps;
   a) separating defibrinated whole blood, whereby a red blood cell fraction and a liquid fraction are formed;
   b) diafiltering the red blood cell fraction to thereby form purified red blood cells; and
   c) lysing the purified red blood cells, thereby forming the lysate of purified red blood cells.

16. The method of claim 15, wherein the whole blood is mechanically defibrinated.

17. The method of claim 15, wherein the whole blood is fractionated by centrifuging the whole blood.

18. The method of claim 15, wherein the purified red blood cells are lysed mechanically.

19. The method of claim 15, wherein the whole blood is bovine whole blood.

20. A method of forming a lysate of purified red blood cells for use in a hemoglobin blood substitute, comprising the steps;
   a) separating defibrinated whole bovine blood by centrifugation, whereby a red blood cell fraction and a liquid fraction are formed;
   b) diafiltering the red blood cell fraction to thereby form purified red blood cells; and
   c) mechanically lysing the purified red blood cells, thereby forming the lysate of purified red blood cells.

* * * * *